United States Patent [19]

Greco

[11] 4,399,310

[45] Aug. 16, 1983

[54] PREPARATION OF 1,3-CYCLIC DIONES BY VAPOR PHASE CYCLIZATION OF DELTA-KETO CARBOXYLIC ACID ESTERS UTILIZING CARRIER CONDENSABLE UNDER AMBIENT CONDITIONS

[75] Inventor: Nicholas P. Greco, Pittsburgh, Pa.

[73] Assignee: Koppers Company, Inc., Pittsburgh, Pa.

[21] Appl. No.: 303,541

[22] Filed: Sep. 18, 1981

[51] Int. Cl.³ .......................................... C07C 45/45
[52] U.S. Cl. ................................................ 568/346
[58] Field of Search ....................... 568/346, 354, 355

[56] References Cited

U.S. PATENT DOCUMENTS

| | | | |
|---|---|---|---|
| 3,932,511 | 1/1976 | Schaafsma et al. | 568/346 |
| 3,950,436 | 4/1976 | Schaafsma et al. | 568/346 |
| 4,018,833 | 4/1977 | Muller et al. | 568/346 |
| 4,028,417 | 6/1977 | Muller et al. | 568/314 |

FOREIGN PATENT DOCUMENTS

| | | | |
|---|---|---|---|
| 6170 | 9/1980 | European Pat. Off. | 568/346 |
| 2448677 | 4/1976 | Fed. Rep. of Germany | 508/346 |
| 2749437 | 5/1978 | Fed. Rep. of Germany | 568/346 |

*Primary Examiner*—James H. Reamer
*Attorney, Agent, or Firm*—Donald M. Mac Kay; J. Timothy Keane; Herbert J. Zeh, Jr.

[57] ABSTRACT

A process is disclosed for making 1,3-cyclic diones by vapor-phase cyclization of delta-keto carboxylic acid esters over a carbon catalyst bed. The delta-keto ester is conveyed through the catalyst bed by a carrier gas characterized by being liquid at 25° C. and having a sufficiently high boiling point that the carrier gas is easily condensable under ambient conditions. The delta-keto ester is highly soluble in the liquid carrier, while the cyclic dione product of the ester has very low solubility in the liquid carrier. Use of the described carrier in vapor-phase cyclization of delta-keto esters allows efficient separation of cyclic dione product and unreacted starting material from the carrier after the cyclization reaction.

17 Claims, No Drawings

PREPARATION OF 1,3-CYCLIC DIONES BY VAPOR PHASE CYCLIZATION OF DELTA-KETO CARBOXYLIC ACID ESTERS UTILIZING CARRIER CONDENSABLE UNDER AMBIENT CONDITIONS

BACKGROUND OF THE INVENTION

1. Field of the Invention

Preparation of cyclic diones by catalytic cyclization of certain delta-keto carboxylic acid esters is well known. Of particular interest herein are process improvements to the vapor-phase cyclization of delta-keto carboxylic acid esters.

2. State of the Art

U.S. Pat. No. 4,028,417 to Muller et al. describes the liquid-phase, two-step preparation of cyclohexane-1,3-dione type compounds by a first step of cyclization of 4-oxocarboxylic acid alkyl esters in the presence of a strong base such as sodium methylate to provide a sodium salt of the cyclohexanedione, and a second step of acidification of the sodium salt to form the cyclohexanedione. The two-step preparation requires an expensive solvent, such as an amide, sulfoxide, sulfone, or glycol dialkyl ether, in which to carry out the cyclization and acidification steps. Moreover, the Muller '417 preparation generates significant quantities of effluent, the recovery and disposal of which is costly.

U.S. Pat. No. 3,932,511 to Schaafsma et al. describes the preparation of cyclohexane-1,3-dione type compounds by vapor-phase cyclization of a delta-keto carboxylic acid ester in a hydrogen-nitrogen carrier gas stream passed over an activated carbon bed. The ester starting material is typically present in the carrier gas in a mole ratio of about 13-to-one carrier gas-to-ester. Recovery of cyclohexane-1,3-dione product and unreacted starting ester from the gas stream requires cooling the gas stream to at least −20° C.

German Offen. No. 2,825,170 of Muller et al. describes the preparation of cyclohexane-1,3-dione type compounds by vapor-phase cyclization of a delta-keto carboxylic acid ester over a catalyst provided by carbon, alumina, or like support, impregnated with salts of Group IIIB or IVB elements. The ester is carried in a vapor state in a gas stream provided by an equimolar mixture of nitrogen and an ethylene glycol ether. Since the cyclohexane-1,3-dione has high solubility in aliphatic ethers, such as ethyleneglycol ether, removal of cyclohexane-1,3-dione product and unreacted keto ester requires a distillation step. In addition to requiring a complex, expensive catalyst, the Muller '170 preparation involves a two-step process for removing cyclic dione product and unreacted delta-keto ester. Firstly, the gas stream must be cooled to condense the ether to a liquid in which the cyclic dione product and keto ester are dissolved; secondly, the liquid ether must be distilled from the cyclic dione and unreacted ester, and distillation must occur at a sufficiently low temperature to remove the ether without destroying the heat-sensitive cyclic dione.

There remains, therefore, a need for a simple catalytic vapor-phase cyclization process for making 1,3-cyclic diones from delta-keto esters requiring no expensive refrigeration or condensing equipment to separate the cyclic dione product from the vapor-phase carrier.

SUMMARY OF THE INVENTION

A process is provided for making a cyclic dione of the general formula

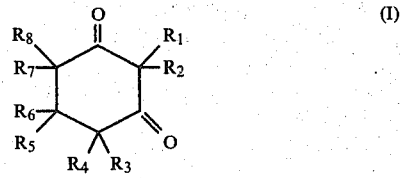

wherein $R_1$ through $R_8$ are selected from hydrogen and alkyl groups of about six carbon atoms, with the proviso that the total number of carbon atoms of $R_1$ through $R_8$ cannot exceed about 24. The process comprises the step of passing a gas stream through a reaction zone containing a carbon catalyst suitable for catalyzing cyclization of a delta-keto ester to form a cyclic dione. The catalyst is characterized in being totally devoid of certain elements deposited on the carbon, such as the Group IIIB and Group IVB elements of the Periodic System. The gas stream comprises a delta-keto ester mixed with or dissolved in a condensable non-reactive carrier. The delta-keto ester has the general formula

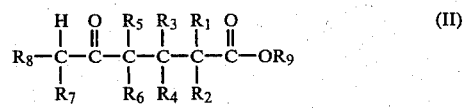

wherein $R_1$ through $R_8$ are defined as before and $R_9$ is selected from alkyl, aryl and alkylaryl groups, with the proviso that the total number of carbon atoms of $R_9$ cannot exceed about 24. The non-reactive carrier is selected such that the delta-keto ester starting material is soluble in the carrier. Also, it is preferred that the carrier be selected such that the cyclic dione product is only slightly soluble or insoluble in the carrier, or be selected such that the dione product is only slightly soluble or insoluble in the selected carrier in combination with unreacted starting ester and alcohol by-products formed during the cyclization reaction. Moreover, a suitable carrier must be liquid at 25° C. under one atmosphere and must have a sufficiently high boiling point that it is condensable from the gas phase at about 25° C. under ambient atmospheric conditions.

The gas stream leaving the reaction zone is condensed to provide a liquid stream containing the cyclic dione product together with some unreacted delta-keto ester starting material and an alcohol formed as a by-product in the cyclization reaction. The carrier material and alcohol by-product are removed from the liquid stream, usually by distillation at reduced pressure, leaving behind cyclic dione product mixed with, or dissolved in, unreacted delta-keto ester. Cyclic dione product may be separated from unreacted ester by crystallization and filtration techniques. Unreacted delta-keto ester may then be recycled into a starting mixture for redelivery to the reaction zone.

One advantage of the process of the invention resides in use of a vapor-phase reaction medium in which the carrier gas is easily condensable into a liquid as compared to carrier gases utilized heretofore. In prior processes, carrier gases such as hydrogen and nitrogen are utilized in a gas stream having relatively high carrier-toester ratios and traveling at high velocity; separation of vaporized products and contaminants from such carrier gases requires cooling of the gas stream to −20° C. or less to allow separation of products from the gas stream. This cooling step must be provided at relatively high cost in terms of refrigeration and condensing equipment and energy requirements. The use of an easily condensable gas as provided in the present process obviates the need for a relatively expensive gas condensing step. Moreover, the process of the invention is advantageous in providing relatively high yields of cyclic dione product formed from delta-keto ester, and in which process little or no harmful by-products are formed.

The process of the invention is particularly suitable for the cyclization of 5-keto-hexanoic acid esters into dihydroresorcinol compounds which, in turn, may be dehydrogenated to resorcinol or substituted resorcinols. More particularly, the process is suitable for continuous vapor phase cyclization of methyl 4-oxocaproate to 3-hydroxy-2-cyclohexene-1-one (which is the enol tautomer of 1,3-cyclohexanedione), which compound may be dehydrogenated into resorcinol, that is, 1,3-dihydroxybenzene.

DETAILED DESCRIPTION OF THE INVENTION

Starting materials for use in the present process comprise delta-ketocarboxylic acid esters (i.e., 5-oxohexanoic acid esters) having the general formula II, above. In particular, $R_1$ through $R_8$ substituents may be provided by hydrogen and lower alkyl groups; methyl, ethyl and propyl groups are preferred. The $R_9$ substituent may be provided by various alkyl groups, whether linear, branched or cyclic, by various aryl groups, whether mono-nuclear, bi-nuclear or polynuclear, and by various mono- or polynuclear alkylaryl groups. Preferred alkyl groups for the $R_9$ substituent include methyl, ethyl, n-propyl, isopropyl, n-butyl, sec-butyl and n-hexyl groups. Typical aryl groups include phenyl and naphthyl groups. A typical alkylaryl group is benzyl.

Esters which may be used as starting materials in the process are 5-oxohexanoic acid esters prepared generally by the reaction of an acrylic acid ester with a suitable alkyl- or aryl-substituted ketone. Useful acrylic acid esters are those having the general formula

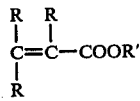

(III)

wherein R may be hydrogen, or an alkyl, aryl, or alkylaryl group, and R' may be an alkyl, aryl, or alkylaryl group. Examples of suitable acrylic acid esters are methyl acrylate, methyl methacrylate, ethyl acrylate, ethyl methacrylate, butyl acrylate, octyl acrylate and dodecyl acrylate. Suitable ketones are those having one or more labile hydrogens in α-position to the ketone carbonyl group. Examples of suitable aliphatic ketones are acetone, methyl ethyl ketone, methyl propyl ketone, diethyl ketone, methyl isopropyl ketone, methyl heptyl ketone, acetyl acetone and acetonyl acetone. Examples of suitable cycloaliphatic ketones are cyclopentanone and cyclohexanone. An example of a suitable alkylaryl ketone is benzyl methyl ketone. Conditions for preparation of these 5-oxohexanoic acid esters are found in U.K. Pat. No. 1,473,184.

Specific delta-keto esters which may be useful in the process are methyl 4-oxocaproate (a.k.a. 5-oxohexanoic acid methyl ester), 5-oxohexanoic acid n-butyl ester, 5-oxohexanoic acid isopropyl ester, 5-oxohexanoic acid isobutyl ester, 4-methyl-5-oxohexanoic acid methyl ester, 5-oxoheptanoic acid methyl ester, 4-methyl-5-oxoheptanoic acid methyl ester, 4-n-propyl-5-oxohexanoic acid methyl ester, 5-oxononanoic acid methyl ester, 5-oxo-4-phenylhexanoic acid methyl ester, and 5-oxo-6-phenylhexanoic acid methyl ester.

A non-reactive, easily-condensable liquid carrier is used to convey the delta-keto ester into a cyclization reactor. The term "non-reactive" characterizes a carrier which is substantially inert with respect to reaction with the delta-keto ester, with the cyclization product, and with the carbon catalyst under conditions of cyclization. The term "easily-condensable" characterizes a carrier having a sufficiently high boiling point that the carrier changes from the vapor state to a liquid under ambient conditions, namely, under about one atmosphere pressure and at about 25° C. It is preferred that the delta-keto ester and the carrier be selected for use in the cyclization process so that delta-keto ester in soluble in the carrier, but so the cyclization product is only slightly soluble, or much less soluble than the ester, in the carrier.

Materials suitable as carriers are liquid at about 25° C. under one atmosphere pressure and may be selected from the following general classes of compounds: lactones, organic acids, organic anhydrides, esters and aromatic hydrocarbons. Examples of suitable lactones are γ-butyrolactone and ε-caprolactone. Examples of suitable organic acids are acetic acid, propionic acid and pelargonic acid. Examples of esters are ethyl acetate, butyl acetate and amyl acetate. Examples of aromatic hydrocarbons are benzene, toluene, o-, m-, p-xylenes, cumene, pseudocumene, ethylbenzene, isodurene and prehnitene.

A reactor suitable for the cyclization reaction is typically a fixed-bed type reactor having a preheater or vaporization zone and a catalysis or reaction zone. The preheater or vaporization zone may be provided by a bed of Pyrex glass beads or similar material capable of being heated and held to a temperature of about 500° C. Adjacent to the vaporization zone is a reaction zone containing a carbon catalyst in a fixed bed mode. The carbon catalyst is usually comprised of particles having diameters in a range from about 0.4 mm to about 1.0 mm, having specific surface area in a range from about 900 m²/g to about 1400 m²/g, and having a pore volume in a range from about 0.8 cc/g to about 1 cc/g. The catalyst bed is typically packed with carbon to a density in a range from about 20 lbs/ft³ to about 30 lbs/ft³ and has a free space in a range from about 12 ml to about 17 ml. Useful carbon catalysts include Filtrasorb No. 300 and No. 400 series carbon catalysts (Calgon Corp., Pittsburgh, Pa.). These catalysts are used as purchased without any modification as to composition. These catalysts are totally devoid of the Group IIIB and Group IVB elements of the Periodic System. Before introduction of the delta-keto ester and carrier into the reactor, the preheater bed and the catalyst reactor are heated to about 400° C. Then hydrogen is passed through the reactor for a period of time, typically about 16 hours, in order to activate the catalyst bed.

The delta-keto ester starting material is dissolved in the liquid carrier to form a solution such that the ester is present in the solution in an amount in a range from about 8 to about 26 mole percent of the liquid solution. A liquid stream containing the carrier and ester is then introduced to the reactor preheater bed usually held at a temperature in a range from 300° C. to about 500° C. in order to vaporize the carrier and ester into a gas stream. Rate of delivery of the liquid stream generally depends upon the dimensions of the reactor. The gas stream enters the activated carbon catalyst bed of the reaction zone under pressure as furnished by the back pressure from the vaporization of the liquid stream in the preheater section. Typically, the temperature of the carbon catalyst bed is held substantially uniformly throughout the bed length in a range from about 350° C. to about 400° C. The gas stream travels through the carbon bed at a liquid hourly space velocity in a range from about 0.13 to about 0.21, with a catalyst contact time in a range from about three seconds to about eight seconds.

After leaving the catalysis zone of the reactor, the gas stream enters a condensing zone. The condensing zone is usually maintained at ambient temperature and atmospheric conditions, namely, at about 25° C. and one atmosphere pressure. It is an advantage of the process of the invention that complicated and expensive refrigeration and condensing equipment are not required for removal of cyclization reaction products from the gas stream. Thus, a simple collecting vessel remote from the heated reactor may be used for condensing the gas stream and receiving the resulting liquid. It is preferred that a carrier be selected such that the delta-keto ester starting material is freely soluble in the carrier while the cyclic dione product is only slightly soluble, or substantially insoluble, in the carrier. After the condensing step the dione product may precipitate or crystallize from the condensed carrier, while unreacted delta-keto ester will desirably remain dissolved in the liquid carrier. In separation of some cyclic diones from the condensed liquid stream, the carrier material is removed from the liquid stream by distillation at reduced pressure, thereby leaving cyclic dione product mixed with or dissolved in unreacted delta-keto ester. Precipitated or crystallized cyclic dione product may then be filtered from the liquid carrier or from unreacted delta-keto ester, as the case may be, and washed with a solvent, typically the same solvent as used for the carrier, and then dried to provide relatively pure cyclic dione product in high yield.

Unreacted delta-keto ester may be recycled continuously into a fresh liquid stream introduced to the cyclization reactor. It has been found that a continuous vapor-phase cyclization process in accordance with the invention is capable of an ultimate yield of cyclic dione product of 100 percent. "Ultimate yield" is defined as per-pass yield of cyclic dione product divided by conversion of delta-keto ester starting material.

The following examples set forth specific embodiments of the invention. The invention is not to be construed, however, as being limited to these embodiments for there are, of course, numerous possible variation and modifications. All parts and percentages of the examples as well as throughout the specification are by weight unless otherwise indicated.

EXAMPLE I

A vertically-oriented Pyrex glass reactor tube 36 inches in length and one inch in diameter was packed with about 44 g of Filtrasorb No. 400 activated carbon (Calgon Corp., Pittsburgh, Pa.) to make a uniformly-dense catalyst bed about ten inches in length and occupying about 97 cc volume. Resting on top of the carbon catalyst bed was a three-inch thick layer of ⅛-inch diameter Pyrex glass beads, which layer provides a preheater bed. The reactor tube was placed in a furnace constructed to receive the reactor tube in a sleeve fitting such that the furnace heated the catalyst and pre-heater beds. Located within upper, middle and lower portions of the catalyst bed were temperature sensing thermocouples. In order to activate the catalyst bed, hydrogen gas was passed through the catalyst bed for a period of about 16 hours with the bed temperature maintained at about 400° C.

After the reactor tube reached equilibrium conditions with a temperature maintained at about 400° C. in the preheater and carbon beds, a liquid mixture containing methyl 4-oxocaproate (MOC) and toluene was pumped into the reactor tube over a period of about five hours at a rate of about 28 ml/hr. The liquid mixture contained 0.08 mole MOC for every 0.62 mole toluene (11.4 mole percent ester-in-liquid stream); for each one-hour pumping period, 18.7 g MOC and 53.4 g toluene were delivered into the reactor tube. When the liquid mixture contacted the glass-bead preheater bed, the mixture immediately vaporized and formed a gas having a back pressure of about 0.3 mm Hg, as measured at the preheater bed. With a catalyst bed free space of 150 ml, the reaction mixture had a catalyst contact time of about 5.2 seconds and a liquid hourly space velocity of 0.21. The product gas stream leaving the reactor tube condensed into a liquid on the unheated portion of the walls of the reactor tube. Condensed liquid was collected in a receiving vessel at room temperature. Gas chromatographic analysis of a sample of condensate collected during the third and fourth hours of the reaction period showed 7.4 wt. % 3-hydroxy-2-cyclohexene-1-one, 73 wt. % toluene, 17.0 wt. % unreacted MOC, and a small amount of methanol by-product; these products correspond to a conversion of 36 mole percent MOC to DHR. No phenol contaminant by-product was detected in the product stream.

The toluene carrier was removed from the condensate by distillation at 50° C. under reduced pressure. Care was taken to maintain the temperature of the condensate below 90° C. during distillation in order to avoid decomposition of the 3-hydroxy-2-cyclohexene-1-one product. Residue from distillation was allowed to cool to room temperature, at which temperature there formed light yellow crystals in contact with an amber-colored liquid. The crystals were separated from the liquid by filtration; then the crystals were pressed to remove residual MOC and washed with toluene; and thereafter the crystals were dried to remove toluene. Analysis of dried crystals showed 98 wt. % 3-hydroxy-2-cyclohexene-1-one and 2 wt. % MOC, which crystals were suitable for use directly in the conversion of 3-hydroxy-2-cyclohexene-1-one into resorcinol by dehydrogenation. The filtrate, containing unreacted MOC and some dissolved 3-hydroxy-2-cyclohexene-1-one, was useful for recycling into the activated carbon bed of the reactor to produce more of this cyclic dione. Based upon analysis of the condensate, the ultimate yield of 3-hydroxy-2-cyclohexene-1-one was 100 percent.

EXAMPLE II

A vertically-oriented Pyrex glass reactor tube 36 inches in length and one inch in diameter was packed with about 44 g of Filtrasorb No. 300 activated carbon (Calgon Corp., Pittsburgh, Pa.) to make a uniformly dense catalyst bed about ten inches in length and occupying about 97 cc volume. Resting on top of the carbon catalyst bed was a three-inch thick layer of ⅛-inch diameter Pyrex glass beads, which layer is provided a preheater bed. The reactor tube was placed in a furnace constructed to receive the reactor tube in a sleeve fitting such that the furnace heated the catalyst and preheater beds. Located within upper, middle and lower portions of the catalyst bed were temperature sensing thermocouples. In order to activate the catalyst bed, hydrogen gas was passed through the catalyst bed for a period of about 16 hours with the bed temperature maintained at about 400° C.

After the reactor tube reached equilibrium conditions with a temperature maintained at about 375° C. in the preheater and carbon beds, a liquid mixture containing methyl 4-oxocaproate (MOC) and toluene was pumped into the reactor tube over a period of about five hours at a rate of about 75 ml/hr. The liquid mixture contained 0.08 mole MOC for every 0.62 mole toluene (11.4 mole percent ester-in-liquid stream); for each one-hour pumping period, 11.5 g MOC and 57 g toluene were delivered into the reactor tube. When the liquid mixture contacted the glass-bead preheater bed, the mixture immediately vaporized and formed a gas having a back pressure of about 0.3 mm Hg, as measured at the preheater bed. With a catalyst bed free space of 150 ml, the reaction mixture had a catalyst contact time of about 5.3 seconds and a liquid hourly space velocity of 0.13. The product gas stream leaving the reactor tube condensed into a liquid on the unheated portion of the walls of the reactor tube. Condensed liquid was collected in a receiving vessel at room temperature. Gas chromatographic analysis of a sample of condensate collected during the third and fourth hours of the reaction period showed 5.1 wt. % 3-hydroxy-2-cyclohexene-1-one, 82 wt. % toluene, 10.3 wt. % unreacted MOC, and a small amount of methanol by-product; these products correspond to a conversion of 39 mole percent MOC to 3-hydroxy-2-cyclohexene-1-one.

The toluene carrier was removed from the condensate by distillation at 50° C. under reduced pressure. Care was taken to maintain the temperature of the condensate below 90° C. during distillation in order to avoid decomposition of the 3-hydroxy-2-cyclohexene-1-one product. The residue from distillation was allowed to cool to room temperature, at which temperature there formed light yellow crystals in contact with an amber-colored liquid. The crystals were separated from the liquid by filtration; then the crystals were pressed to remove residual MOC and washed with toluene; and thereafter the crystals were dried to remove toluene. Analysis of dried crystals showed 98 wt. % 3-hydroxy-2-cyclohexene-1-one and 2 wt. % MOC, which crystals were suitable for use in the conversion of 3-hydroxy-2-cyclohexene-1-one into resorcinol by dehydrogenation. The filtrate, containing unreacted MOC and some dissolved 3-hydroxy-2-cyclohexene-1-one, was useful for recycling into the activated carbon bed of the reactor to produce more of this cyclic dione. Based upon analysis of the condensate, the ultimate yield of 3-hydroxy-2-cyclohexene-1-one was 100 percent. No phenol contaminant by-product was detected in the product stream.

EXAMPLES III–V

The vapor phase cyclization of methyl 4-oxocaproate to 3-hydroxy-2-cyclohexene-1-one was repeated in three additional experiments performed substantially in accordance with the procedures of Example I. Essential experimental parameters and results are summarized in Table I.

TABLE I

| | Vapor Phase Cyclization of Methyl 4-Oxocaproate (MOC) to 3-Hydroxy-2-cyclohexene-1-one in Toluene | | | | | | | | |
|---|---|---|---|---|---|---|---|---|---|
| | | | | | | Phenol Contaminant | 3-Hydroxy-2-cyclohexene-1-one | | Reaction Period | Feed[2] Wt. % |
| Example No. | Filtrasorb Catalyst[1] | Catalyst Temp., °C. | MOC LHSV | Contact Time (sec) | MOC Conversion (mole %) | Ultimate Yield (mole %) | Yield per pass (mole %) | Ultimate Yield (mole %) | at Equilibrium (hrs.) | MOC in Toluene |
| I | #400 | 400 | 0.21 | 5.2 | 36 | 0 | 36 | 100 | 2 | 26.3 |
| II | #300 | 375 | 0.13 | 5.3 | 39 | 0 | 39 | 100 | 2 | 16.8 |
| III | #300 | 375 | 0.21 | 5.4 | 20 | 0 | 20 | 100 | 2 | 26.3 |
| IV | #300 | 350 | 0.13 | 5.6 | 17 | 0 | 17 | 100 | 4 | 16.8 |
| V | #300 | 400 | 0.21 | 5.2 | 33 | 0 | 33 | 100 | 2 | 26.3 |

[1]$H_2$ passed through catalyst bed at 400° C. for 16 hours before reaction period.
[2]MOC-in-toluene average feed rate = 0.7 mole/hr.

Although specific examples of the instant invention have been set forth hereinabove, it is not intended that the invention be limited solely thereto, but is to include all the variations and modifications falling within the scope of the appended claims.

What is claimed is:

1. A process for making a cyclic dione of the general formula

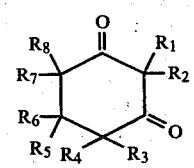

wherein $R_1$–$R_8$ are selected from hydrogen and alkyl groups of up to about 6 carbon atoms, with the proviso that the total number of carbon atoms of $R_1$–$R_8$ cannot exceed 24, said process comprising:
 passing a gas stream through a reaction zone containing a carbon catalyst suitable for cyclization of a delta-keto ester to form a cyclic dione, said gas stream comprising a delta-keto ester and a condensable non-reactive carrier, said delta-keto ester having the general formula

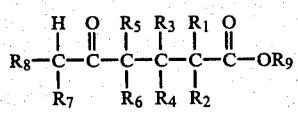

wherein $R_1$–$R_8$ are defined as before and $R_9$ is selected from an alkyl, aryl and alkylaryl groups, with the proviso that the total number of carbon atoms of $R_9$ cannot exceed 24, said non-reactive carrier selected from a lactone, an organic acid, an organic anhydride, an ester, and an aromatic hydrocarbon; with the further proviso that substantially all of said carrier has a sufficiently high boiling point so that said carrier is a liquid at 25° C. and under one atmosphere pressure, whereby the gas stream may be easily condensed and cyclic dione product subsequently separated from the carrier and from unreacted delta-keto ester.

2. The process of claim 1 wherein the temperature of said carbon bed is at least about 300° C.

3. The process of claim 1 wherein said cyclic dione is a dihydroresorcinol and the delta-keto ester is a 5-ketohexanoic acid ester.

4. The process of claim 1 wherein said cyclic dione is 3-hydroxy-2-cyclohexene-1-one, and the delta-keto ester is methyl 4-oxocaproate.

5. The process of claim 1 wherein said non-reactive carrier is selected such that the cyclic dione has a solubility under standard conditions of less than about 10 volume percent in the selected non-reactive carrier.

6. The process of claim 1 wherein said non-reactive carrier is an aromatic hydrocarbon.

7. The process of claim 6 wherein said aromatic hydrocarbon is toluene.

8. The process of claim 1 wherein said delta-keto ester has a concentration in said gas stream in a range from about 6 mole percent to about 30 mole percent.

9. The process of claim 1 further comprising the step of
    passing a hydrogen gas stream through a carbon bed to provide an activated carbon bed suitable for catalyzing cyclization of a delta-keto ester into a cyclic dione.

10. The process of claim 1 further characterized by the delta-keto ester having a liquid hourly space velocity in a range from about 0.05 to about 3.0.

11. The process of claim 1 further characterized by the delta-keto ester having a carbon bed contact time in a range from about 0.2 second to about 30 seconds.

12. The process of claim 1 further comprising the step of
    condensing said gas stream after passing through the carbon bed within a condensing zone having a temperature in a range from about 20° C. to about 50° C., to provide a liquid stream containing cyclic dione product, unreacted delta-keto ester and said carrier.

13. The process of claim 12 further characterized by the step of
    recovering cyclic dione product from the liquid stream by cooling the liquid stream to a temperature sufficient to crystallize the cyclic dione, whereby crystallized cyclic dione may then be filtered from the liquid stream and dried.

14. A process for making 3-hydroxy-2-cyclohexene-1-one by vapor-phase cyclization of methyl 4-oxocaproate, said process comprising:
    (a) passing hydrogen gas through a carbon bed to provide an activated carbon catalyst suitable for catalyzing the cyclization of methyl 4-oxocaproate to 3-hydroxy-2-cyclohexene-1-one;
    (b) passing a gas stream in contact with said activated carbon catalyst, said gas stream comprising methyl 4-oxocaproate and an easily-condensable non-reactive carrier, said carrier selected from a lactone, an organic acid, an organic anhydride, an ester and an aromatic hydrocarbon, with the proviso that said carrier is liquid at 25° C. under one atmosphere pressure; and
    (c) condensing said gas stream within a condensing zone having a temperature in a range from about 20° C. to about 50° C. to provide a liquid stream containing 3-hydroxy-2-cyclohexene-1-one, unreacted methyl 4-oxocaproate and said carrier,
whereby 3-hydroxy-2-cyclohexene-1-one may be recovered from the liquid stream by subsequent steps of cooling and filtering the liquid stream.

15. The process of claim 14 wherein said non-reactive carrier is an aromatic hydrocarbon.

16. The process of claim 15 wherein said aromatic hydrocarbon is an alkyl benzene.

17. The process of claim 16 wherein said alkyl benzene is toluene.

* * * * *